United States Patent [19]

Greubel et al.

[11] Patent Number: 5,237,997
[45] Date of Patent: Aug. 24, 1993

[54] METHOD OF CONTINUOUS MEASUREMENT OF BLOOD PRESSURE IN HUMANS

[75] Inventors: Waldemar Greubel, Taufkirchen; Albrecht A. C. von Müller, Pöcking; Hubertus von Stein; Rudolf Wieczorek, both of München, all of Fed. Rep. of Germany

[73] Assignee: Vectron Gesellschaft Für Technologieentwicklung und Systemforschung mbH, Fed. Rep. of Germany

[21] Appl. No.: 576,404

[22] PCT Filed: Mar. 9, 1989

[86] PCT No.: PCT/DE89/00152
§ 371 Date: Nov. 8, 1990
§ 102(e) Date: Nov. 8, 1990

[87] PCT Pub. No.: WO89/08424
PCT Pub. Date: Sep. 21, 1989

[30] Foreign Application Priority Data

Mar. 9, 1988 [DE] Fed. Rep. of Germany ....... 3807672

[51] Int. Cl.$^5$ ............................................. A61B 5/021
[52] U.S. Cl. ................................... 128/672; 128/687; 128/696; 128/715
[58] Field of Search ............... 128/672, 687, 691, 696, 128/715, 713, 664, 633, 689

[56] References Cited

U.S. PATENT DOCUMENTS

| | | | |
|---|---|---|---|
| 3,628,525 | 12/1971 | Polanyi et al. | 128/633 |
| 3,985,121 | 10/1976 | Hellenbrand | 128/689 |
| 4,030,485 | 6/1977 | Warner | 128/667 |
| 4,201,222 | 5/1980 | Haase | 128/634 |
| 4,278,095 | 7/1981 | Lapeyre | 128/689 |
| 4,703,758 | 11/1987 | Omura | 128/672 |
| 4,869,262 | 9/1989 | Orr et al. | 128/672 |
| 4,907,596 | 3/1990 | Schmid et al. | 128/672 |
| 4,913,150 | 4/1990 | Cheung et al. | 128/633 |
| 4,926,867 | 5/1990 | Kanda et al. | 128/633 |
| 5,054,493 | 10/1991 | Cohn et al. | 128/672 |

Primary Examiner—Lee S. Cohen
Assistant Examiner—Kevin Pontius
Attorney, Agent, or Firm—Klarquist, Sparkman, Campbell, Leigh and Whinston

[57] ABSTRACT

In a process for continuous measurement of blood pressure, the mean blood pressure is derived from the measured pulse wave duration. The other blood pressure parameters are obtained by combination with an opto-electrical determination of blood volume density in a typical manner at the ear lobes. An initial individual basic calibration of the blood pressure values is carried out by a conventional method. In addition, a continuous automatic optoelectronic post-calibration is carried out. The measuring sensors are preferably a pair of ear clips and ECG electrodes or a photoelectric sensor. The method can be used to particular advantage in prevention and diagnosis.

11 Claims, 3 Drawing Sheets

METHOD OF CONTINUOUS MEASUREMENT OF BLOOD PRESSURE IN HUMANS

FIELD OF THE INVENTION

The invention relates to a method for the continuous, non-invasive measurement of blood pressure in humans.

BACKGROUND OF THE INVENTION

All known blood-pressure measuring instruments which used in practice and are non-invasive use the measuring method according to Riva-Rocci/Korotkoff (RR-method) or, instead of the Korotkoff microphone, the oscillation of the pressure in an elastic cuff in a modified way. This applies to instruments for manual use as well as to automated instruments which are offered as mobile blood pressure monitors measuring for 24 hours a day. The main disadvantages of blood pressure monitors of this kind, which one basically can also have on one's person, are that they are very unpleasant for the patient in the long run due to the repeated interruption of the blood circulation and that the consequently long time intervals at which the blood pressure is taken do not allow a continuous measurement.

A further known fact is that the speed of the pulse waves allows a certain access to the blood pressure. In measuring the speed of the pulse waves or pulse-wave running time (PWL) the running time of the pulse wave caused by every heartbeat is measured, wherein either the time difference between the R-peak of the electrocardiogram (ECG) and the pulse's arrival at a peripheral artery is measured or the time difference between two pulses whose distance to the heart is different is detected by means of mechanical or optical sensors. The pulse-wave running time determined in this way correlates with mean blood pressure values to an intraindividually large extent. The main disadvantage of this method is that a separate measurement of diastolic and systolic pressure values is not possible on principle.

Furthermore, there are measuring instruments on the market which, using photoelectric means, continuously determine alterations in the blood quantity in the ear lobes, which varies with the pulse, but this determination is only qualitative and very approximate. These so-called ear pulse measuring instruments (OPM), however, which have basically been known for a long time, only serve to determine the pulse frequency.

Other proposals for the non-invasive, continuous measurement of blood pressure which work in that a sensor is placed unremovably and in an exact fashion over a discrete artery (e.g. brachial artery in the arm) practically fail because of their being much too sensitive to movement artefacts.

BRIEF SUMMARY OF THE INVENTION

Although human blood pressure is one of the most important physiological measures with regard to circulation and of great significance in prevention, diagnosis and monitoring before and after an operation, it is a problem in all of these fields to measure the blood pressure continuously and in a non-surgical fashion.

Hence the problem to be solved is to provide a blood-pressure measuring process by means of which the blood pressure can be measured continuously, non-surgically and with the necessary accuracy, especially the systolic, diastolic and mean blood pressure. A further problem to be solved is to avoid the said disadvantages of the known measuring instruments based on the RR-method. The problem of their sensitivity to movement artefacts is to be solved as well.

According to the invention, this problem is essentially solved by the method defined in patent claim 1. Further useful developments of the invention can be seen from the subclaims.

Blood volume density in the sense of the present invention can be defined as the blood volume—which periodically varies with the pulse and is influenced by regulations within the body—per unit volume of tissue in a part of the body's tissue having a dense network of blood vessels (e.g. ear lobes).

The main advantages of the invention are that a continuous, non-invasive measurement of the blood pressure is not only possible in hospital, but also in one's normal surroundings, even while sleeping, that the measuring sensors, that is to say ear clip and ECG electrodes, physically affect the patient to a negligible extent, that one can have the measuring system comfortably on one's person because it is very small and light, that the system's susceptibility to movement artefacts has been reduced to a minimum, because measurement is not carried out at a discrete artery, and that the measuring system can be produced at much lesser costs than systems according to the state of the art.

Basically, all measuring systems recording pulse, in the case of which a measurement signal taken at the ear lobe is proportional to the blood volume density and/or the blood pressure, can be used as sensors of ear pulse measuring instruments for determining the arterial blood volume density proportional to the blood pressure.

In principle, every area of the skin which is well supplied with blood can be used as location to measure the arterial blood volume density, with the acral areas of the skin (fingers, toes, ear lobes) being especially suitable for placing sensors of course.

In order to eliminate the influence of the variable oxygen-saturation of the blood on the sensor signal of the ear pulse measuring instrument preferably a wave length of IR-light $\lambda$ is chosen, which results from the point of intersection of the spectral transmission for reduced and oxygenated blood, the so-called isobestic point (e.g. $\lambda = 805$ nm).

In cases where the determination of the pulse wave duration by means of ECG electrodes does not supply satisfying results, a suitable miniature microphone, which is fixed over the heart by means of adhesive tape, is used instead of the ECG electrode. The microphone then serves to determine the systole (first cardiac sound).

In an especially preferred further development of the invention a sensor consisting of light emitting diode and photodiode, to be placed on a certain area of chest or back near the heart, can also be used as a reference sensor for sensing the pulse wave near the heart instead of ECG electrodes or miniature microphones. In this case, by analogy with the sensor of the ear pulse measuring instrument, the light of the light emitting diode is scattered at the fine network of the blood vessels, the scattered light recorded by the photodiode, and thus the moment at which the pulse wave passes the sensor is accurately sensed. What is decisive here is that the area of the skin on which the sensor is placed is supplied with blood by an intercostal artery being as close to the heart as possible. For this sensor close to the heart the location on the chest or the back is—considering the anotomical course of the blood vessels—to be chosen in such a way that the running time of the pulse wave from the heart to the sensor close to the heart is minimized and hence the difference of the running time of the pulse wave between the sensor close to the heart and the ear pulse sensor is maximized. This preferred embodiment is especially accurate and its susceptibility to disturbances particularly low.

An additional way of further reducing movement artefacts, but also other disturbing influences, is to provide both ear lobes with an ear pulse measuring instrument each. By comparing the signals received from both ear lobes, e.g. using a coincidence circuit, disturbances of many kinds can be eliminated.

BRIEF DESCRIPTION OF THE DRAWINGS

In the following an embodiment of the invention is described in detail with reference to the drawing. The drawing shows.

DETAILED DESCRIPTION OF THE INVENTION (Two) ECG electrodes are placed on the patient's chest over the heart. The sensor of the ear pulse measuring instrument is clipped on to the ear lobe by means of an ear clip or additionally fastened with adhesive tape. The sensor of the ear pulse measuring instrument has two functions: A small source of light with a suitable wave length sends light through the ear lobe. The transmission of the ear lobe, which proportionally varies with the blood pressure, is measured by a photodiode. Moreover, the arrival of the pulse wave at the ear lobe, sensed relatively to the systole by means of the ECG signal, can immediately be seen from the time behavior of the transmission. This means that the pulse-wave running time for the distance heart/ear lobe is determined.

Before the beginning of the permanent measurement an individual calibration curve is plotted for each patient, which indicates the relation between the pulse-wave running time and the mean blood pressure $p_m$ belonging to it and which is determined according to the long-known method using cuffs. Since this relation is almost linear, approximately three measuring points, corresponding to the same amount of necessary stages of circulatory exercise in calibration, are sufficient for its representation.

Figure 1:
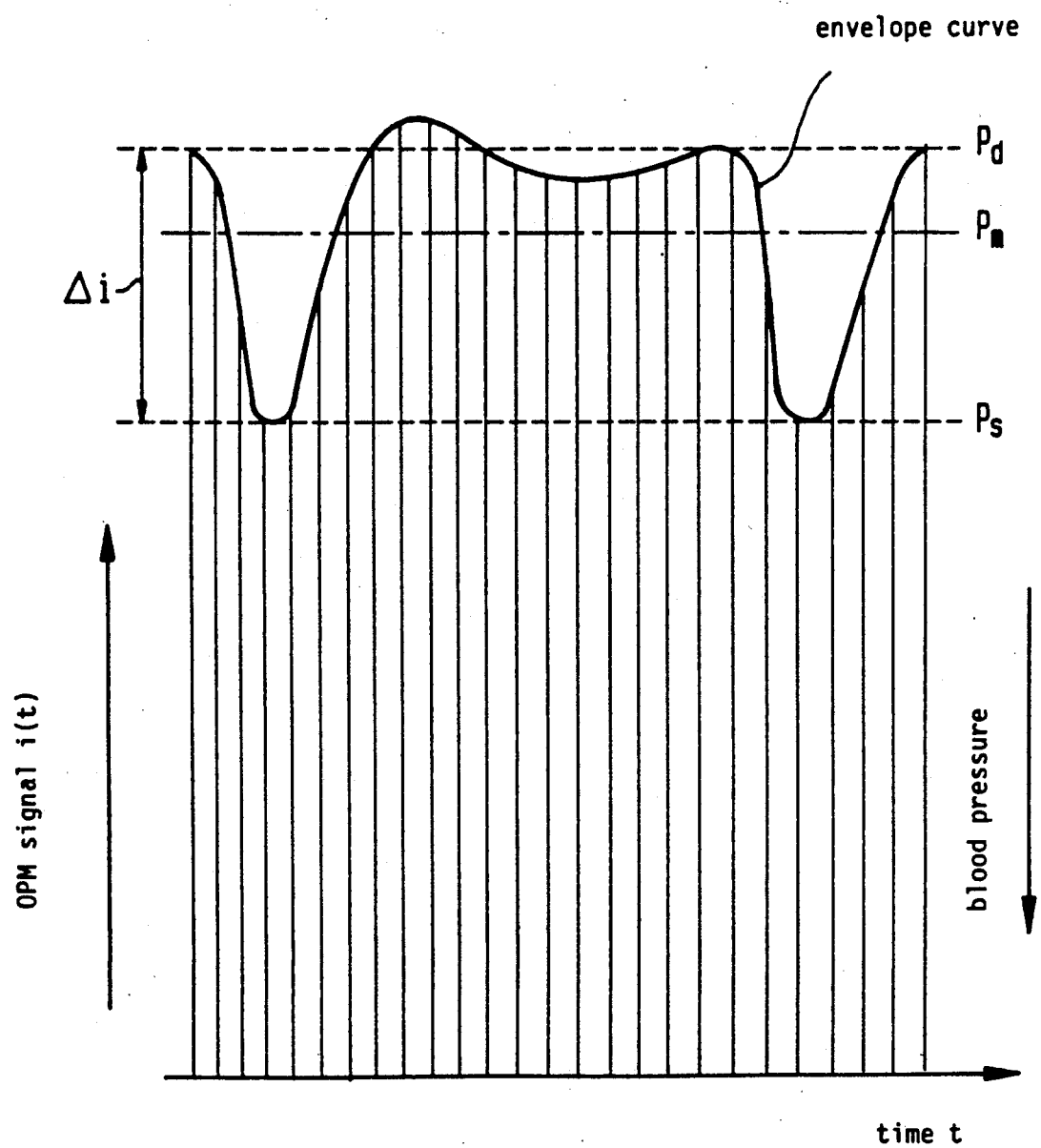
FIG. 1 a diagram of the time behavior of the output signal of the ear pulse measuring instrument of the blood-pressure measuring instrument working on the basis of the process according to the invention, FIG. 2 a schematic representation of the blood-pressure measuring instrument working according to the process of the invention and FIG. 3 a sectional view of the ear clip of the blood-pressure measuring instrument according to the invention as a semi-schematic representation.

For further explanation, FIG. 1 schematically shows the course of the photocurrent i(t) at the photodiode of the ear pulse measuring instrument, with the source of light being a pulsed (infra-red) light diode in this example. At the right-hand margin of the diagram the corresponding blood pressure values are indicated (mean $p_m$, systolic $p_s$ and diastolic pressure $p_d$). In practice, the following is valid:

$$P_m = P_d + f \cdot (p_s - P_d) \qquad (equation\ 1)$$

with $f = \frac{1}{3}$ being valid for peripheral arteries in general. In cases of doubt f can easily be determined specifically for the individual patient.

Since according to equation 1 there is a linear relation between the three blood pressure values $p_m$, $p_s$ and $p_d$ in practice, it becomes clear that either $p_m$, $p_s$ or $p_d$ can alternatively be correlated to the pulse-wave running time (PWL) in calibration. In any case it is to be noted that only one of the two independent blood pressure values can be obtained by measuring the pulse-wave running time. The second independent blood pressure value is determined by means of the photocurrent curve of the ear pulse measuring instrument as follows:

The envelope curve of the photocurrent signal i(t) in FIG. 1 helps to illustrate the procedure. In this curve the blood pressure difference $\Delta p = p_s - p_d$ corresponds to the signal difference $\Delta i$. If, at the beginning of the blood-pressure measurement, one measurement of $p_s$ and $p_d$ according to the Riva/Rocci method is carried out at a certain moment, $\Delta i$ can be correlated to $\Delta p$, that is to say, the curve of the photocurrent can be converted into blood pressure values for a limited period of time (at least for a few seconds), and at the same time the zero point for the blood-pressure scale can be permanently determined (FIG. 1, right-hand margin). As, however, the correlation of photocurrent values to blood pressure values changes due to vasomotoric and other regulations within the body in the course of time, an automatic recalibration of this correlation is carried out according to the invention e.g. by using the value of $p_d$, which is permanently determined by means of the pulse-wave running time, in order to recalibrate the photocurrent curve according to the blood pressure values, so that the systolic blood pressure can then be directly read off from the photocurrent value belonging to $p_s$. One can proceed in an analogous way, if one has alternatively correlated the blood pressure values $p_s$ or $p_m$ in the calibration curve specific of the patient to the pulse-wave running time. When calibrating the photocurrent curve of the ear pulse measuring instrument into blood pressure values, use can be made of equation 1.

The said permanent recalibration, which is carried out automatically by electronic means is necessary for the following reasons:

In the dense arterial vessel system of the ear lobe, signal changes $\Delta i$ can typically result firstly by vasodilations proportional to the blood pressure and synchronous to the pulse, and secondly be influenced by slow vasomotoric and other changes in the amount of capillaries the blood flows through.

If e is the extinction of the IR-light (sum of light absorbed and scattered), q(t) the pulsating cross-section of the vessel and $n_{Cap}$ the amount of capillaries through which blood flows at a respective moment, then the following proportionality is true: $e \sim q(t) \cdot n_{Cap}$. $n_{Cap}$ is changing slowly. Changes of $n_{Cap}$ are taken into account through the said automatic recalibration.

Figure 2:
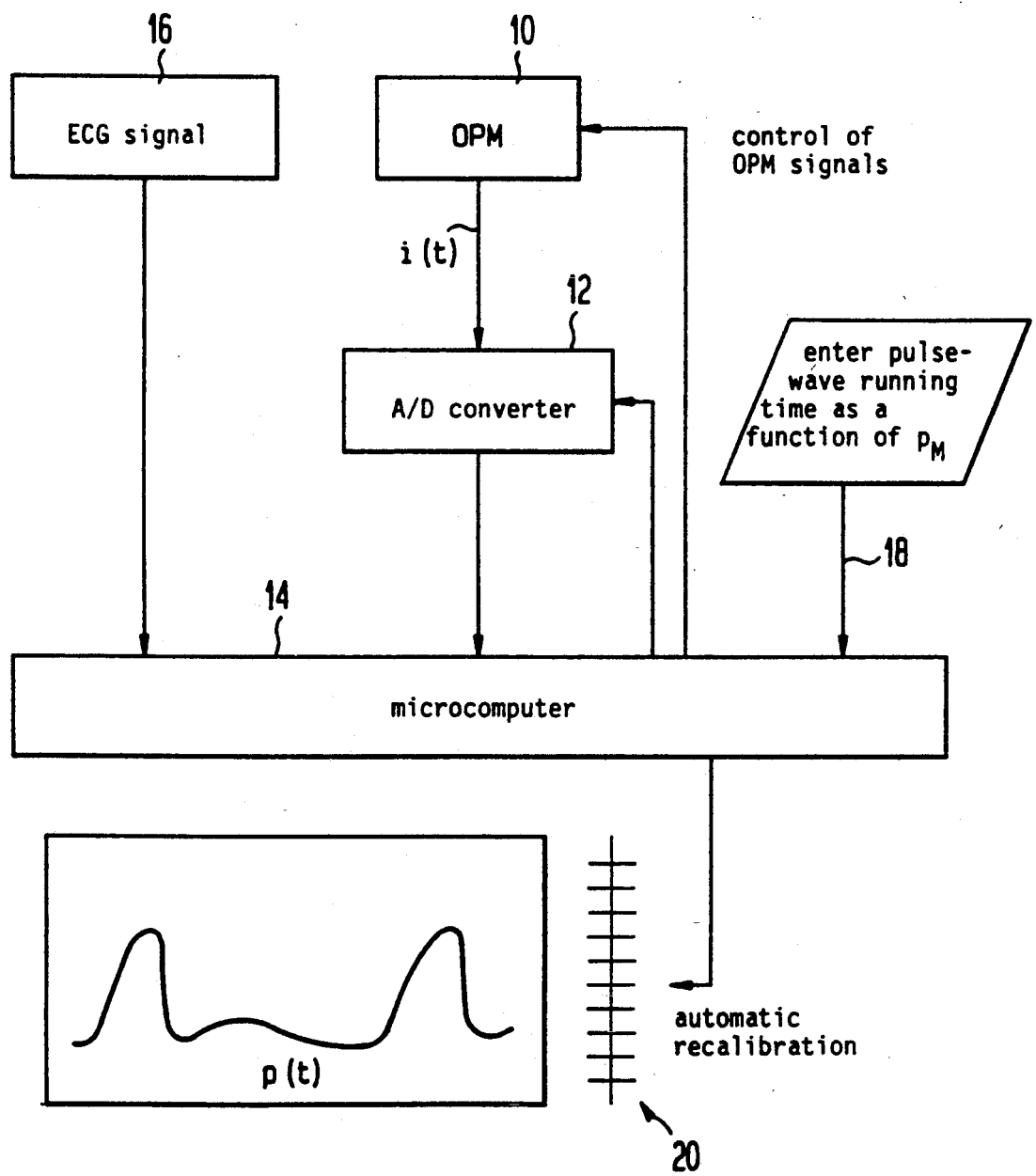

The block diagram in FIG. 2 makes the structure of the blood-pressure measuring system plain, wherein it is sufficient to outline the paths the signals take between the single components and to leave details to the expert.

The signal i(t) outlined in FIG. 1 moves from the ear pulse measuring instrument 10 into the analog/digital converter 12. The digitalized signal is sent to the microcomputer 14 to be processed. The A/D converter 12 receives control signals from the microcomputer 14. Moreover, the microcomputer 14 also controls all signals it receives from the ear pulse measuring instrument 10. The signals from the reference sensor 16 needed to sense the start of the pulse wave (exemplarily symbolized as an ECG signal in FIG. 2) are sent directly to the microcomputer 14. In addition, the calibration curve specific of the patient is entered into the microcomputer 14 via the line 18 and stored in the microcomputer 14 (in FIG. 2 the case was chosen that the pulse-wave running time was determined as a function of $p_m$). This calibration curve is used by the microcomputer to permanently convert the running time of every pulse wave into the blood pressure value chosen in the respective case. Moreover, in FIG. 2 a further task of the microcomputer 14 is outlined, that is, the automatic recalibration of the photocurrent curve into blood pressure values at 20.

Figure 3:
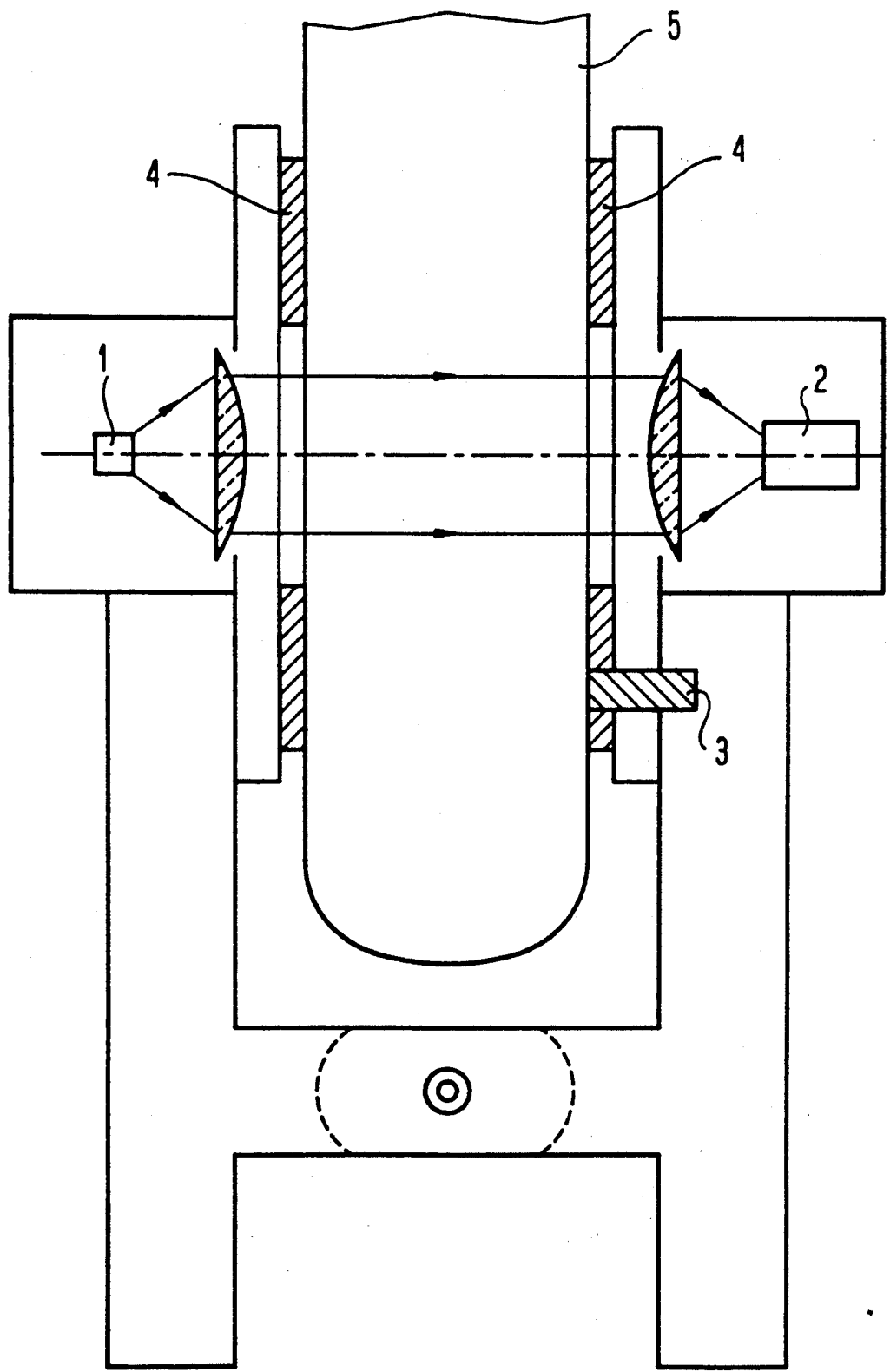

The cross-section of an embodiment of a sensor of an ear pulse measuring instrument in the form of an ear clip is represented in FIG. 3. In this representation 1 designates a light emitting diode, 2 a photodiode and 3 an integrated temperature probe. The ear clip clipped to the ear lobes is well fixed by means of ring-shaped adhesive tape 4 at both sides of the ear lobe 5. The temperature probe 3 has skin contact with the ear lobe. Taking the temperature serves to additionally check alterations in the blood volume density of the ear lobe, which have to be monitored permanently as described.

Moreover, both ear lobes may be provided with one ear pulse measuring instrument each. the measuring signals of the two pulse measuring instruments may be compared electronically in order to eliminate disturbances of various kinds. For example, the two measurement signals may be received by a coincidence circuit which suppress all signals not measured at both ear lobes at the sane, and thus rates them as artefacts.

We claim:

1. A method of continuously measuring blood pressure in humans, and permanently measuring a pulse-wave running time of every pulse wave of a pateint's body, comprising the steps of:
    determining one of three blood pressure values comprising systolic, diastolic or mean blood pressure by measuring the pulse-wave running time;
    fixing an ear pulse measuring instrument to the patient's ear lobe and using the ear pulse measuring instrument to measure the pulse-wave running time between the patient's heart and the ear lobe;
    converting the pulse-wave running time into blood pressure values by using a calibration curve specific of each patient, which indicates the pulse-wave running time as a function method for measuring the blood pressure in order to establish this calibration curve;
    continuously determining an arterial blood volume density proportional to the blood pressure by means of an output signal of the ear pulse measuring instrument;
    determining the blood pressure using the output signal of the ear pulse measuring instrument after the output signal has been calibrated by comparing it with the blood-pressure measuring process according to Riva-Rocci;
    continuously recalibrating the output signal of the ear pulse measuring instrument in order to take into account vasomotoric and other regulations within the body, with the continuous recalibration step performed by electronic means permanently correlating the blood pressure value determined by measuring the pulse-wave running time to the respective output signal of the ear pulse measuring instrument, and thus permanently recalibrating the output signal of the ear pulse measuring instrument as a whole into blood pressure values;
    providing the patient's other ear lobe with a second ear pulse measuring instrument having an output signal; and
    comparing the output signals of the two pulse measuring instruments with each other electronically in order to eliminate disturbances of various kinds.

2. Method according to claim 1, characterised in that recalibration is carried out in that for certain constant blood pressure values the corresponding measurement signals are recorded and the blood pressure values corrected on the basis of alterations of these signals.

3. A method according to claim 1, further including the steps of:
    before the beginning of the continuous blood-pressure measurement, measuring the systolic and diastolic blood pressure values according to the Riva-Rocci method;
    calculating a pressure difference $\Delta p$ from the measured systolic and diastolic blood pressure values; and
    correlating the pressure difference $\Delta p$ to the difference $\Delta i$ of the output signal corresponding to he diastolic value and the output signal corresponding to the systolic value of the ear pulse measuring instrument.

4. A method according to claim 1 further including the step of before the beginning of the continuous blood-pressure measurement, measuring the pulse-wave running time depending on several blood pressure values in order to establish the calibration curve specific of the patient.

5. A method according to claim 1 further including the step of using for measuring the pulse-wave running time a photo-electric sensor, which is placed on an area of the skin at the patient's chest or back which is near the heart and is supplied with blood by an intercostal artery close to the heart.

6. A method according to claim 1 further including the step of using ECG electrodes over the heart to measure the pulse-wave running time.

7. A method according to claim 1 further including the step of using for measuring the pulse-wave running time a miniature microphone fixed over the heart to sense a first cardiac sound.

8. A method according to claim 1 wherein the fixing step comprises using a pulsed infra-red light diode to send light through the ear lobe and that the transmission of the ear lobe is measured by a photodiode.

9. A method according to claim 8 further including the step of avoiding influences due to variable oxygen saturation of the blood by choosing a wave length of IR-light near an isometric point for the infra-red light diode.

10. A method according to claim 1, further including the steps of:
    receiving the two measurement signals of the two pulse measuring instruments with a coincidence circuit; and
    suppressing with the coincidence circuit all signals not measured at both ear lobes at the same time and thus rating them as artefacts.

11. A method according to claim 1 further including the step of continuously taking the body-temperature at the ear lobe.

* * * * *